United States Patent [19]

Kawamura et al.

[11] 4,124,646

[45] Nov. 7, 1978

[54] PROCESS FOR PRODUCING THIOANISOLE

[75] Inventors: Masao Kawamura, Akashi; Masakazu Hatta, Kakogawa; Nobuhiro Koune, Kobe; Nobuyuki Kitagishi, Takasago, all of Japan

[73] Assignee: Seitetsu Kagaku Co., Ltd., Japan

[21] Appl. No.: 737,623

[22] Filed: Nov. 1, 1976

[30] Foreign Application Priority Data

Nov. 5, 1975 [JP] Japan .................................. 50/133345
Dec. 5, 1975 [JP] Japan .................................. 50/145280

[51] Int. Cl.² ........................................... C07C 148/00
[52] U.S. Cl. ................................................ 260/609 E
[58] Field of Search .................................... 260/609 E

[56] References Cited

U.S. PATENT DOCUMENTS 2,745,878  /1956  Mavity ................................. 260/609
3,450,771  /1969  Dombro ............................... 260/609
3,470,257  /1969  Sparks ................................. 260/609

OTHER PUBLICATIONS

Hansch et al., JACS, 72 (1950), 4810.
Vogel, JCS, (1948), 1820.

*Primary Examiner*—Lewis Gotts
*Assistant Examiner*—Molly C. Eakin
*Attorney, Agent, or Firm*—Pollock, Vande Sande & Priddy

[57] ABSTRACT

Industrially useful alkylphenyl sulfides are produced in high yield from phenyl mercaptan as a raw material by reaction of the phenyl mercaptan with an alkyl alcohol or dialkyl ether, or alkyl mercaptan or dialkyl sulfide having 1 to 4 carbon atoms as a novel alkylating agent at an elevated temperature, for example, 150° to 600° C, in a gaseous phase.

6 Claims, No Drawings

PROCESS FOR PRODUCING THIOANISOLE

This invention relates to a novel process for producing alkylphenyl sulfides.

Alkylphenyl sulfides are industrially useful compounds as raw materials for medicaments, agricultural chemicals, etc., and above all thioanisole is a very useful compound having wide applications to herbicides, insecticides and various solvents.

Heretofore, the alkylphenyl sulfides have been usually produced by alkylating phenyl mercaptan with an alkylating agent such as dialkyl sulfate, alkyl halide, alkyl amine, etc., and above all the alkylation with dialkyl sulfate has been regarded as preferable on account of higher yield than those with other alkylating agents (A. I. Voger: JCS 1948 1820). However, these alkylations are all carried out in liquid phase, which requires complicated steps for separating the reaction products, or the separated waste liquor or the like offers a problem, when the prevention of environmental pollution is taken into account. Especially, the process using dialkyl sulfate is still not an advantageous one for industrial application because the dialkyl sulfate is expensive, and because the dialkyl sulfate is so strongly irritating that its handling is quite inconvenient, etc.

The present inventors have made an extensive study of a process for producing alkylphenyl sulfide by a gaseous phase reaction that is advantageous in the industrial practice, and as a result have found that the alkylphenyl sulfides can be formed by reacting phenyl mercaptan with at least one of alkylating agents represented by the general formula, $R_1OR_2$, wherein $R_1$ is an alkyl group having 1 to 4 carbon atoms, and $R_2$ is a hydrogen atom, or an alkyl group having 1 to 4 carbon atoms, or at least one of alkylating agents represented by the general formula, $R_1SR_2$, wherein $R_1$ represents an alkyl group having 1 to 4 carbon atoms, and $R_2$ represents a hydrogen atom or an alkyl group having 1 to 4 carbon atoms at an elevated temperature condition in a gaseous phase. When there is a catalyst, for example, activated alumina, in the reaction system, it has been found that said reaction is considerably promoted, and the present invention has been established based on the foregoing findings.

An object of the present invention is to provide a novel process for producing alkylphenyl sulfides in good yield with industrial advantages, using phenyl mercaptan and a low cost alkylating agent. The present invention is characterized by using an alkylating agent represented by the general formula, $R_1OR_2$ or $R_1SR_2$, wherein $R_1$ represents an alkyl group having 1 to 4 carbon atoms, and $R_2$ represents a hydrogen atom or an alkyl group having 1 to 4 carbon atoms, which has been so far unknown as the alkylating agent for phenyl mercaptan, and conducting the alkylation reaction in a gaseous phase. More particularly, the characteristics of the present invention are that the present alkylating agent is cheap, by-products are hardly produced, yields of alkyl phenyl sulfides are high, and the process is very simple and thus is very economically advantageous, as compared with the conventional process.

The alkylating agent represented by the general formula, $R_1OR_2$, or $R_1SR_2$, where $R_1$ represents an alkyl group having 1 to 4 carbon atoms, and $R_2$ represents a hydrogen atom or an alkyl group having 1 to 4 carbon atoms include, for example, alkyl alcohols such as methyl alcohol, ethyl alcohol, n-propyl alcohol, i-propyl alcohol, n-butyl alcohol, i-butyl alcohol, tert.butyl alcohol; dialkyl ethers such as dimethyl ether, diethyl ether, dipropyl ether, dibutyl ether, methylethyl ether, ethylpropyl ether; alkyl mercaptan such as methyl mercaptan, ethyl mercaptan, n-propyl mercaptan, n-butyl mercaptan, tert.butyl mercaptan; dialkyl sulfides such as dimethyl sulfide, diethyl sulfide, dipropyl sulfide, dibutyl sulfide, etc.

In the present invention, the alkyl alcohols and the alkyl ethers can be used alone or in a mixture of at least two thereof, and the alkyl mercaptans and dialkyl sulfides can be used alone or in a mixture of at least two thereof, as the alkylating agent.

In the case of dialkyl ether or dialkyl sulfide, the process will be more simple, and its industrial practice will be easier, when said $R_1$ and $R_2$ are identical with each other, as in the case of dimethyl ether, diethyl ether, dimethyl sulfide, or diethyl sulfide.

A mode of practising the present invention will be described below.

A molar ratio of the alkyl group of an alkylating agent, $R_1OR_2$ or $R_1SR_2$, to the phenyl group of phenyl mercaptan, is in a range of 0.1 to 10, preferably 0.5 to 5. The molar ratio of more than 10 has no considerable influence upon the yield, and a larger amount of the alkylating agent must be uselessly handled, making the process uneconomical. Moreover, the larger amount of the alkylating agent is liable to increase the steps of purification to remove the byproducts. On the other hand, the molar ratio of less than 0.1 naturally decreases the yield, and a larger amount of phenyl mercaptan must be uselessly handled, making its industrial practice unsuitable. Therefore, an appropriate molar ratio of the alkylating agent to phenyl mercaptan should be selected in said range. For example, in the case of using phenyl mercaptan, and methanol, dimethyl ether, methyl mercaptan or dimethyl sulfide as the alkylating agent, the yield of the desired product thioanisole reaches a maximum, that is, 96% or more, based on the fed phenyl mercaptan, when the molar ratio of the alkyl group of the alkylating agent to the phenyl group of phenyl mercaptan of 1.0 to 2.0 is selected in view of the above considerations.

Reaction temperature for carrying out the alkylation of the present invention must be high enough to maintain said two raw materials in a gaseous phase, but not so high as to decompose the raw materials and the reaction product, and is usually in a range of 150° to 600° C., preferably 200° to 500° C. In most cases, the alkylation is carried out under the atmospheric pressure, but, if desired, can be carried out under an increased or reduced pressure. To obtain a good contact of the two raw materials, heat-resistant materials, such as porcelain rings, can be filled in a reactor before the alkylation, if desired.

It is desirable to conduct the alkylation of the present invention in the presence of a catalyst, which is very effective for promotion of the reaction. Examples of the catalyst include activated alumina, silica, silica-alumina, activated acid clay, zeolite, diatomaceous earth, other silica-alumina compositions, activated carbon, etc. Usually the shape of the catalyst is granular, and its sizes are in a range of 2 mm to 10 mm. These catalysts can be used alone or in a mixture of at least two thereof, or together with an additive of improving the strength or activity of the catalyst.

The catalytic reaction in the gaseous phase of the present invention is carried out at said reaction temperature usually in a tubular reactor at a space velocity of 20 to 2000 hr$^{-1}$, though depending upon the selected reaction temperature.

At the elevated temperature as in the present invention, especially in the presence of the catalyst dialkyl ether and water are formed from alkyl alcohol, and reversibly alkyl alcohol from dialkyl ether and water.

In the case of alkyl mercaptan and dialkyl sulfide, di-alkyl sulfide and hydrogen sulfide are similarly formed from alkyl mercaptan, and reversibly alkyl mercaptan from dialkyl sulfide and hydrogen sulfide. Therefore, even if, for example, methyl alcohol, or dimethyl ether, or a mixture thereof is used to react with phenyl mercaptan, the alkylation proceeds smoothly without producing any by-product, and thus thioanisole is formed in high yield.

The mechanism of the present invention has not been fully clarified yet, but it seems that the reaction is most probably an ionic one, as often seen in the catalytic reaction based on alumina catalyst.

Purification of the reaction product is carried out in the following manner. When an alkyl alcohol or a dialkyl ether represented by $R_1OR_2$ is used as the alkylating agent, the resulting alkylphenyl sulfide and water, and a portion of unreacted phenyl mercaptan and unreacted alkyl alcohol or dialkyl ether are liquified by cooling the reaction product after the reaction. However, when an alkyl alcohol having more carbon atoms is used, a decomposition gas such as olefins is partially by-produced. The liquified product is immediately separated into an aqueous layer and an oil layer due to a difference in gravity, and the unreacted raw materials can be readily recovered by distilling the oil layer, and the desired product alkylphenyl sulfide of high purity can be obtained at the same time. The recovered unreacted raw materials can be recycled to the process as the raw materials.

On the other hand, when an alkyl mercaptan or dialkyl sulfide represented by $R_1SR_2$ is used as the alkylating agent, the desired product alkylphenyl sulfide, and unreacted phenyl mercaptan, and alkyl mercaptan or dialkyl sulfide are liquefied by cooling the reaction product, and hydrogen sulfide is separated. Especially when an alkyl mercaptan having more carbon atoms is used, a hydrogen sulfide gas containing the decomposition gas such as olefins is separated. Therefore, the alkylphenyl sulfide and the unreacted raw materials are separated from each other by distilling the liquefied product, and the recovered unreacted raw materials can be recycled to the process as the raw materials. On the other hand, hydrogen sulfide gas can be used as a raw material for producing alkyl mercaptan and dialkyl sulfide.

According to the present invention, side reaction products are hardly produced, and all the unreacted raw materials can be recycled to the process and reused. Thus, an overall yield is very high. Furthermore, the reaction is carried out in a gaseous phase, and therefore the process itself is simplified, and a continuous operation is easily carried out, making the process suitable for industrial scale mass production and economically advantageously operable. Still furthermore, no treatment is necessary for the waste liquor as an origin of environmental pollution, as encountered in the liquid phase reaction.

Further advantages of the present invention are mentioned below, referring to the case of producing thioanisole through reaction of phenyl mercaptan with methyl alcohol and/or dimethyl ether as an alkylating agent. The thioanisole yield based on phenyl mercaptan can reach 96% or more by selecting appropriate reaction conditions, and the reaction product can be readily separated into an aqueous layer and an oil layer by cooling the reaction product. The oil layer contains a small amount of the unreacted raw materials, but more than 95% by weight of the oil layer is thioanisole, and the thioanisole yield, based on the reacted phenyl mercaptan, reaches a surprisingly high value such as 99%. By distilling the oil layer, a fraction of unreacted phenyl mercaptan and successively a fraction of thioanisole can be obtained. The recovered unreacted phenyl mercaptan is recycled to the process as the raw material. The water layer separated from the reaction product contains only a very small amount of methyl alcohol, and thus can be discarded as such. High yield in the reaction, less side reaction products, that is, the oil layer component separated from the reaction product being comprised substantially of the desired product thioanisole, possibility of purification simply by distillation to obtain a high purity product, etc. each mean much advantage in the industrial practice of the present invention.

Now, the present invention will be described in detail below, referring to Examples, but the present invention is never restricted by these Examples.

EXAMPLE 1

A mixture consisting of 24.2% by weight of methanol, and 75.8% by weight of phenyl mercaptan (molar ratio 1.1) was fed at an hourly rate of 145 g, to a stainless steel preheater, 25 mm in inner diameter and 40 mm in length, filled therein with 150 ml of porcelain rings, 5 mm in diameter, and preheated to about 280° C. The resulting gas mixture was passed through a stainless steel reactor, 40 mm in inner diameter and 400 mm in length, filled therein with 150 ml of Neobead C-4 (trademark of spherical activated alumina, 4 mm in. diameter, made by Mizusawa Kagaku K.K., Japan). The reactor was heated in an electric oven, and the temperature of the catalyst bed was maintained at 300° ± 10° C. The gas leaving the reactor was cooled to about 30° C. to obtain a reaction mixture consisting of an oil layer and an aqueous layer. After the continuous reaction for 3 hours, 374.5 g of the oil layer and 58.5 g of the water layer were obtained by decantation. It was found by gas chromatographic analysis that the oil layer contained 356.5 g of thioanisole and 10 g of unreacted phenyl mercaptan, yield of thioanisole was 96% (the yield is based on the fed phenylmercaptan, and the same yield basis applies to the Examples which follow). On the other hand, the water layer was water containing a very small amount of dimethyl ether and methyl alcohol.

The oil layer was distilled in a packed glass column, 30 mm in diameter, filled therein with porcelain Rasching rings, 3 mm in diameter, up to a packing height of 500 mm, whereby 20 g of phenyl mercaptan containing methyl alcohol and thioanisole, and 341 g of thioanisole having a purity of more than 99% by weight and a boiling point of 76°–77° C./10 mm Hg were obtained. The phenyl mercaptan containing thioanisole could be reused as the raw material.

EXAMPLE 2

The reaction was carried out in the same manner as in Example 1, except that gaseous dimethyl ether was used in place of methyl alcohol, 370 ml of silica-alumina catalyst in tablet forms, 4 mm in diameter × 4 mm in length, N631 (H) (a trademark of the product made by Nikki Kagaku K.K., Japan) was filled in the reactor in place of the activated alumina catalyst, and the temperature of the catalyst bed was maintained at 350° C. Dimethyl ether and phenyl mercaptan were fed to the reactor at hourly rates of 46 g and 110 g, respectively, (molar ratio 2), and after 3 hours from the start of feeding, 375 g of an oil layer and 27 g of an aqueous layer were obtained. It was found by gas chromatographic analysis of the oil layer that the oil layer contained 358 g of thioanisole and 10 g of unreacted phenyl mercaptan. The yield of thioanisole was 96%.

EXAMPLE 3

The reaction was carried out in the same manner as in Example 1, except that a mixture consisting of 29.5% by weight of ethyl alcohol and 70.5% by weight of phenyl mercaptan (molar ratio 1) was fed to the preheater at an hourly rate of 156 g, and the amount of catalyst was changed to 200 ml. After 1 hour from the start of feeding, the resulting reaction product was subjected to decantation, whereby 140 g of an oil layer was obtained. It was found by the gas chromatographic analysis of the oil layer that the oil layer consisted of phenyl mercaptan and thiophenetole, and contained 112 g of thiophenetole. The yield of thiophenetole was 81%.

EXAMPLE 4

The reaction was carried out in the same manner as in Example 1, except that n-propyl alcohol and phenyl mercaptan were fed to the reactor at hourly rates of 48 g and 72.5 g, respectively, (molar ratio 1.2). After 1 hour from the start of the reaction, the reaction product was subjected to decantation, whereby 89 g of an oil layer was obtained. It was found by the gas chromatographic analysis of the oil layer that the oil layer contained 60 g of n-propylphenyl sulfide. The yield of n-propylphenyl sulfide was 60%.

EXAMPLE 5

The reaction was carried out in the same manner as in Example 1, except that n-butyl alcohol and phenyl mercaptan were fed to the reactor at hourly rates of 59 g and 72.5 g, respectively (molar ratio 1.5). After 1 hour from the start of feeding, the reaction product was subjected to decantation, whereby 102 g of an oil layer was obtained. It was found by the gas chromatographic analysis of the oil layer that the oil layer contained 60 g of n-butylphenyl sulfide. The yield of n-butylphenyl sulfide was 55%.

EXAMPLE 6

A mixture consisting of 22.5% by weight of dimethyl sulfide and 77.5% by weight of phenyl mercaptan (molar ratio 1) was fed to a stainless steel preheater, 25 mm in inner diameter and 400 mm in length, filled therein with 150 ml of porcelain rings, 5 mm in diameter, and preheated to about 350° C.

The resulting gaseous mixture was passed through a stainless steel reactor, 40 mm in inner diameter and 400 mm in length, filled therein with 370 ml of Neobead C-4 (a trademark of spherical activated alumina, 4 mm in diameter, made by Mizusawa Kagaku K.K., Japan). The reactor was heated in an electric oven, and the temperature of the catalyst bed was maintained at 400° C. ± 10° C. The product gas leaving the reactor was cooled to about 30° C., and after 4 hours from the start of feeding, 488 g of condensate was obtained. It was found by the gas chromatographic analysis of the condensate that the condensate contained 280 g of thioanisole. The yield of thioanisole was 56%.

The condensate was distilled in a packed glass column, 30 mm in diameter, filled therein with porcelain Raschig rings, 3 mm in diameter, up to a packing height of 500 mm, whereby 170 g of phenyl mercaptan containing a small amount of dimethyl sulfide and thioanisole, and 240 g of thioanisole having a boiling point of 60°-61.5° C./5 mm Hg were obtained. The recovered phenyl mercaptan containing dimethyl sulfide and thioanisole could be used again as the raw materials for the reaction.

EXAMPLE 7

The reaction was carried out in the same manner as in Example 6, except that gaseous methyl mercaptan was used (molar ratio 2) in place of dimethyl sulfide, the amount of the catalyst was changed to 150 ml, and the preheating temperature and reaction temperature were maintained at 300° C. and 350° ± 10° C., respectively. Methyl mercaptan and phenyl mercaptan were fed to the reactor at hourly rates of 96 g and 110 g, and 118 g of the condensate was obtained after 1 hour from the start of feeding.

It was found by the gas charomatographic analysis of the condensate that the condensate contained 49.2 g of thioanisole. The yield of thioanisole was 40%.

EXAMPLE 8

The reaction was carried out in the same manner as in Example 6, except that a mixture consisting of 29.0% by weight of diethyl sulfide and 71.0% by weight of phenyl mercaptan (molar ratio 1) was fed to the reactor at an hourly rate of 77.5 g, and the amount of the catalyst was changed to 150 ml. After 1 hour from the start of feeding, 65 g of condensate was obtained.

It was found by the gas chromatographic analysis of the condensate that the condensate contained 35 g of ethylphenyl sulfide. The yield of ethylphenyl sulfide was 50%.

EXAMPLE 9

Methyl alcohol and phenyl mercaptan were preheated to 300° C. and passed through the same reactor as in Example 1, but filled therein with 400 ml of porcelain rings in place of the catalyst, 5 mm in diameter and 5 mm in length, at hourly rates of methyl alcohol of 25 g and phenyl mercaptan of 58 g (molar ratio 1.5). The reaction temperature was maintained at 500° C. ± 10° C., and after 1 hour from the start of feeding, 81 g of reaction product was obtained.

It was found by the gas chromatographic analysis of the reaction product that the reaction product contained 7.5 g of thioanisole. The yield of thioanisole was 12%.

EXAMPLE 10

Methyl mercaptan and phenyl mercaptan were preheated to about 450° C., and passed through the same reactor as in Example 6, but filled with 400 ml of porcelain rings, 5 mm in diameter and 5 mm in length, in place of the catalyst, at hourly rates of methyl mercaptan of 16 g and phenyl mercaptan of 37 g (molar ratio 1). The reaction temperature was maintained at 500° ± 10° C., and 39 g of condensate was obtained after 1 hour. It was found by the gas chromatographic analysis of the condensate that the condensate contained 4.5 g of thioanisole. The yield of thioanisole was 11%.

What is claimed is:

1. A process for producing thioanisole which comprises reacting phenyl mercaptan with at least one alkylating agent selected from the group consisting of methyl alcohol, dimethyl ether, methyl mercaptan, and dimethyl sulfide wherein both said phenyl mercaptan and said alkylating agent are in the gaseous phase in the presence of a catalyst selected from the group consisting of alumina, alumina-silica, silica and activated carbon for producing said thioanisole at an elevated temperature.

2. A process for producing thioanisole which comprises reacting phenyl mercaptan with at least one of methyl alcohol and dimethyl ether as an alkylating agent in a molar ratio of methyl group of the alkylating agent to phenyl group of the phenyl mercaptan of 0.5:1 to 5:1 at a temperature of 200° to 500° C. wherein both said phenyl mercaptan and said alkylating agent are in the gaseous phase in the presence of a catalyst selected from the group consisting of alumina, alumina-silica, silica, and activated carbon for producing said thioanisole.

3. A process for producing thioanisole which comprises reacting phenyl mercaptan with at least one of methyl mercaptan and dimethyl sulfide as an alkylating agent in a molar ratio of methyl group of the alkylating agent to phenyl group of the phenyl mercaptan of 0.5:1 to 5:1 at a temperature of 200° to 500° C. wherein both said phenyl mercaptan and said alkylating agent are in the gaseous phase in the presence of a catalyst selected from the group consisting of alumina, alumina-silica, silica and activated carbon for producing said thioanisole.

4. A process according to claim 1, wherein the reaction temperature is in a range of 150° to 600° C.

5. A process according to claim 1, wherein the molar ratio of alkyl group of the alkylating agent to phenyl group of the phenyl mercaptan is 0.1:1 to 10:1.

6. A process according to claim 1, wherein the reaction is carried out at a space velocity of 20 to 2000 $hr^{-1}$.

* * * * *